US007100620B2

(12) United States Patent
Fung

(10) Patent No.: US 7,100,620 B2
(45) Date of Patent: Sep. 5, 2006

(54) NAIL CARE SYSTEM

(75) Inventor: Kam Fai Fung, Hong Kong (CN)

(73) Assignee: Conair Corporation, Stamford, CT (US)

( * ) Notice: Subject to any disclaimer, the term of this patent is extended or adjusted under 35 U.S.C. 154(b) by 135 days.

(21) Appl. No.: 10/633,328

(22) Filed: Aug. 1, 2003

(65) Prior Publication Data

US 2004/0065336 A1 Apr. 8, 2004

Related U.S. Application Data

(60) Provisional application No. 60/400,751, filed on Aug. 2, 2002.

(51) Int. Cl.
*A45D 29/18* (2006.01)
*A45D 29/20* (2006.01)

(52) U.S. Cl. ........................................ 132/73.5; 132/75
(58) Field of Classification Search ............... 132/73.6, 132/73, 73.5, 75, 75.3, 75.8, 76.5, 74.5, 76.4, 132/75.6; D28/60, 61, 73; 55/473; 601/15–17
See application file for complete search history.

(56) References Cited

U.S. PATENT DOCUMENTS

| D158,223 | S | | 4/1950 | Shubert |
| 3,134,383 | A | | 5/1964 | Thompson |
| 3,613,696 | A | * | 10/1971 | Paule et al. ................. 132/73.6 |
| 4,137,926 | A | * | 2/1979 | Pao ........................... 132/73.6 |
| 4,359,060 | A | | 11/1982 | Walker |
| D278,367 | S | * | 4/1985 | Sussman ..................... D28/61 |
| 4,979,523 | A | * | 12/1990 | Grimm ...................... 132/73.5 |
| 5,139,036 | A | | 8/1992 | Pickard |
| 5,339,477 | A | * | 8/1994 | Warner et al. ............... 15/97.1 |
| 5,787,903 | A | * | 8/1998 | Blackshear ................. 132/73.5 |
| 6,035,860 | A | | 3/2000 | Mombourquette |
| 6,640,811 | B1 | * | 11/2003 | Cho .......................... 132/73.6 |
| 6,647,988 | B1 | * | 11/2003 | Christianson .............. 132/73.5 |

FOREIGN PATENT DOCUMENTS

JP 2000316629 A * 11/2000

OTHER PUBLICATIONS

International Search Report dated Nov. 26, 2004.

* cited by examiner

*Primary Examiner*—John J. Wilson
*Assistant Examiner*—Robyn Doan
(74) *Attorney, Agent, or Firm*—Lawrence Cruz; Steven A. Garner

(57) ABSTRACT

There is provided a self-contained nail care system having a base housing for storing a powered hand tool, and at least a rotary motion adapter head and a linear motion adapter head for use with the hand tool. The base housing stores the hand tool. The base housing has a nail dryer, an integrated manicure bowl, and integrated UV light and/or other types of heat source.

7 Claims, 8 Drawing Sheets

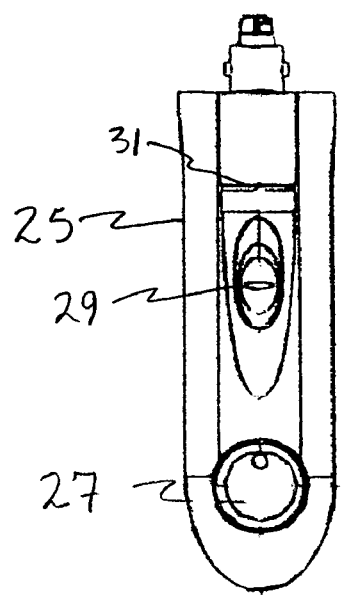
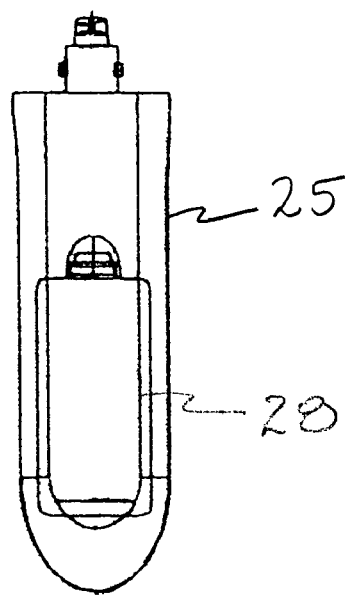
FIG. 6A
FIG. 6B

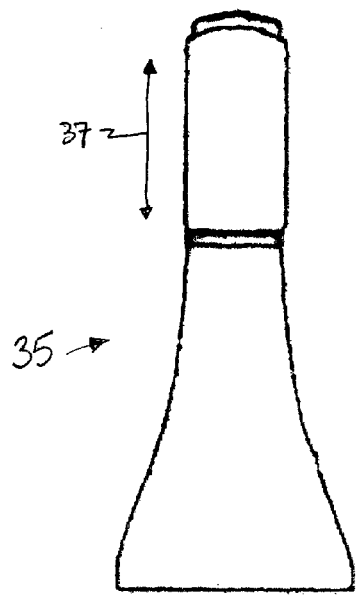
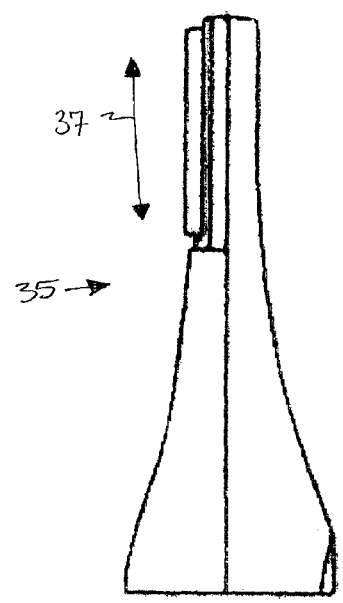
FIG. 7A  FIG. 7B
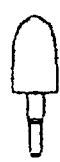
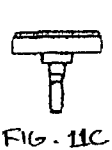
FIG. 11A  FIG. 11B  FIG. 11C  FIG. 11D
FIG. 11E  FIG. 11F  FIG. 11G

NAIL CARE SYSTEM

CROSS-REFERENCE TO RELATED APPLICATIONS

This application is related to U.S. Provisional Patent Application "NAIL CARE SYSTEM", Ser. No. 60/400,751 filed on Aug. 2, 2002, for Kam Fai Fung.

BACKGROUND OF THE INVENTION

1. Field of the Invention

The present invention relates to nail care. More particularly, the present invention relates to a nail care system having a compact housing. The housing has a removable tray and conveniently stores a powered hand tool, a number of adapter heads for use with the powered hand tool, and a number of nail care attachments that interface with the power heads.

2. Description of the Related Art

In the prior art, there are known nail care systems and devices for providing a variety of nail care tools (manual and powered) and storage cases for housing the nail care tools. Generally, the prior art devices that incorporate nail care tools and a storage case for the tools provide a compartment for storing an elongated hand tool in a substantially horizontal position that is neither compact nor particularly functionally other than merely storing the nail care tool. Also, the prior art powered hand tools employ a rotary drive mechanism for rotating nail care attachments. Consequently, the prior art devices tend to be limited to providing rotary motion nail care tooling and have a storage case/housing that is bulky and space-consuming.

Therefore, there exists a need to provide a full-featured, compact, self-contained nail care system having a powered hand tool that provides at least a rotary and linear motion nail care tooling and other functionality in addition to storage of the powered hand tool.

SUMMARY OF THE INVENTION

It is an object of the present invention to provide a nail care system having a base housing that stores the powered hand tool and attachments, wherein the housing is vertically upstanding to minimize the footprint thereof.

It is another object of the present invention to provide such a nail care system having at least a rotary motion head and a linear motion adapter head for being powered by the hand tool.

It is still a further object of the present invention to provide such a nail care system having a removable manicure bowl incorporated into a cavity of the housing.

It is still a further object of the present invention to provide such to a nail care system having a dryer provided in a cavity of the base housing.

It is yet another object of the present invention to provide such to a nail care system having a light source provided in or on the hand tool for illuminating the workspace of the hand tool.

The above and other objects, advantages, and benefits of the present invention will be understood by reference to following detailed description and appended sheets of drawings.

BRIEF DESCRIPTION OF THE DRAWINGS

FIG. 6A is a front view of the hand tool of FIGS. 1 and 2;

FIG. 6B is a rear view of the powered hand tool of FIGS. 1 and 2, including, inter alia, a battery compartment door;

FIG. 7A is a front view of a linear motion adapter head for the hand tool FIGS. 1 and 2;

FIG. 7B is a side view of a linear motion adapter head for interfacing with the hand tool of FIGS. 1 and 2;

FIGS. 11A through 11D are depictions of various nail care attachments for interfacing with the rotary motion adapter head and hand tool of FIGS. 1 and 2; and FIGS. 11E through 11G are depictions of various nail care tools for interfacing with the linear motion adapter head and hand tool of FIGS. 1 and 2.

DETAILED DESCRIPTION OF THE INVENTION

Figure 1:
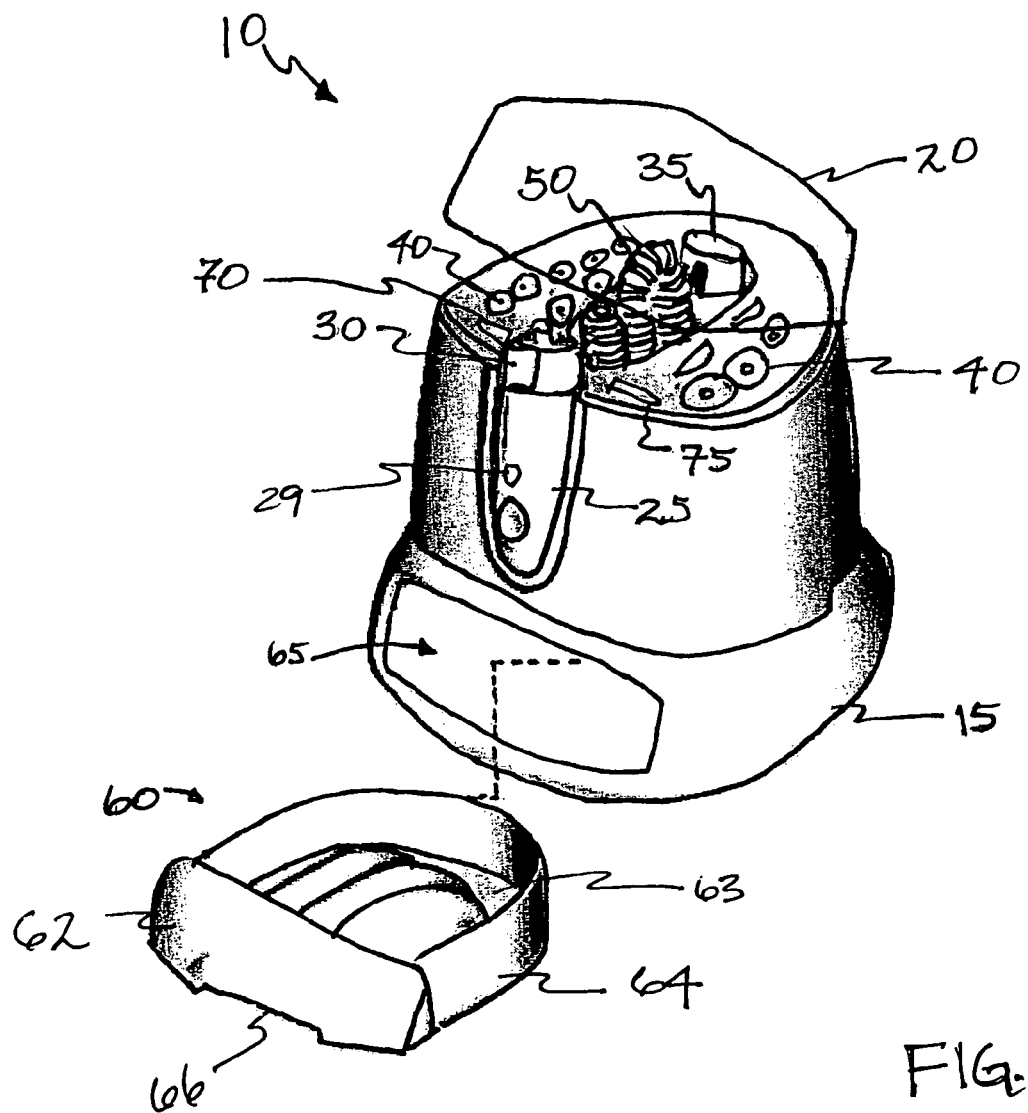
FIG. 1 is a perspective view of a nail care system having a base housing for storing a hand tool, at least a rotary motion adapter head and a linear motion adapter head for use with the hand tool, a number of nail care attachments, and a manicure bowl.

Referring to the drawings and in particular FIGS. 1 through 5, there is provided a nail care system generally represented by reference numeral 10. Nail care system 10 has a base and/or housing 15. As shown, base housing 15 preferably has an upright, vertical configuration. That is, base housing 15 is preferably taller than it is wide. Accordingly, base housing 15, and consequently nail care system 10, is compact in size.

Base housing 15 defines therein a compartment or cavity 65. A lid 20, preferably (though not necessarily) transparent or frosted and hingedly connected, is provide for enveloping at least the top of nail care system 10 to provide a measure of protection from the environment.

In one aspect of the present invention, a manicure bowl 60 for providing a support surface while performing various manicure related treatments, is stored in and substantially concealed by base housing 15. Manicure bowl 60 includes a front wall 62 and an upstanding side wall 64 that cooperates with a bottom floor 63, to define an interior space capable of retaining a liquid therein. Front wall 62 is preferably at least partially translucent, thereby enabling a visual determination of whether fluid is contained is manicure bowl 60 without the need of removing manicure bowl 60 from base housing 15. Floor 63 is preferably contoured to provide a hand supporting surface that comfortably supports and separates the fingers of the hand placed thereupon. Thus, manicure bowl 60 provides at least the dual functions of (1) a liquid bath container for submersion and/or soaking of the hand in the liquid contained therein, and (2) a support surface for air drying the hand and nails.

Manicure bowl 60 may be conveniently and unobtrusively stored in compartment 65 of base housing 15. As shown, front wall 62 may include a handhold 66 for facilitating the selective removal of manicure bowl 60 from base housing 15.

Base housing 15 also provides a number of storage compartments 40 for storing various nail care tool attachments. Referring to FIGS. 11A to 11G, the various nail care attachments may include, though not limited to, the exemplary nail polishers, shapers, and buffers, depicted therein, including a cuticle pusher as shown in FIG. 11E.

The particular number of nail care attachments accommodated and stored in base housing 15 may vary. For example, base housing 15 may facilitate the storage of seven, ten, a dozen, or more nail care attachments.

Base housing 15 also provides storage for a powered hand tool 25. Hand tool 25 can be powered from an external power source such as a residential or commercial AC power outlet. An AC adapter cord (not shown) for connecting nail care system 10 to the AC power outlet may be conveniently stored in cord storage compartment 80 when not in use and/or during transport. The AC adapter cord is connected to nail care system 10 via a power jack 85. Nail care system 10 preferably includes circuitry for accommodating regional power (i.e., voltage and frequency) standards found throughout the world.

Referring to FIGS. 6A and 6B, it is noted that in a preferred embodiment, hand tool 25 may optionally be powered by a power source internal to base housing 15 such a rechargeable battery (not shown). In this instance, base housing 15 preferably has a battery compartment 28 for accepting a battery to power, for instance, a nail dryer discussed herein below. Hand tool 25 can also have a battery compartment for accepting a battery therein for powering hand tool 25.

Power can be transmitted to hand tool 25 by a electrical connections, such as an insulated coiled cord 50 as shown in FIG. 1. Coiled cord 50 is used to provide an electrical connection to hand tool 25 from the power source via power jack 85 and base housing 15, thereby obviating the need to house the power source or related circuitry such as a transformer in hand tool 25.

In an aspect of the present invention, the electrical connection between hand tool 25 and coiled cord 50 may provide both power and control signal connections between hand tool 25 and base housing 15. Control signal communication may be communicated between hand tool 25 and base housing 15 via a wireless communication protocol such as infrared, RF, etc., utilizing transceivers located in hand tool 25 and base housing 15.

Figure 8A:
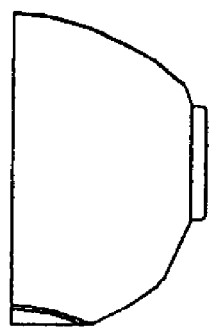
FIG. 8A is a side view of a rotary motion head for interfacing with the hand tool of FIGS. 1 and 2.
Figure 8B:
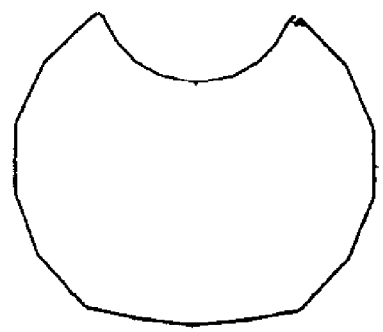
FIG. 8B is a bottom view of a rotary motion adapter head for interfacing with the hand tool of FIGS. 1 and 2.

In an aspect of the present invention, hand tool 25 converts the electrical signal from the power source to a mechanical force. The mechanical force is provided to one of the multiple adapter heads of the present invention. Preferably, the adapter heads include at least a rotary motion adapter head 30 (FIGS. 7A and 7B) and a linear motion adapter head 35 (FIGS. 8A and 8B).

Figure 2:
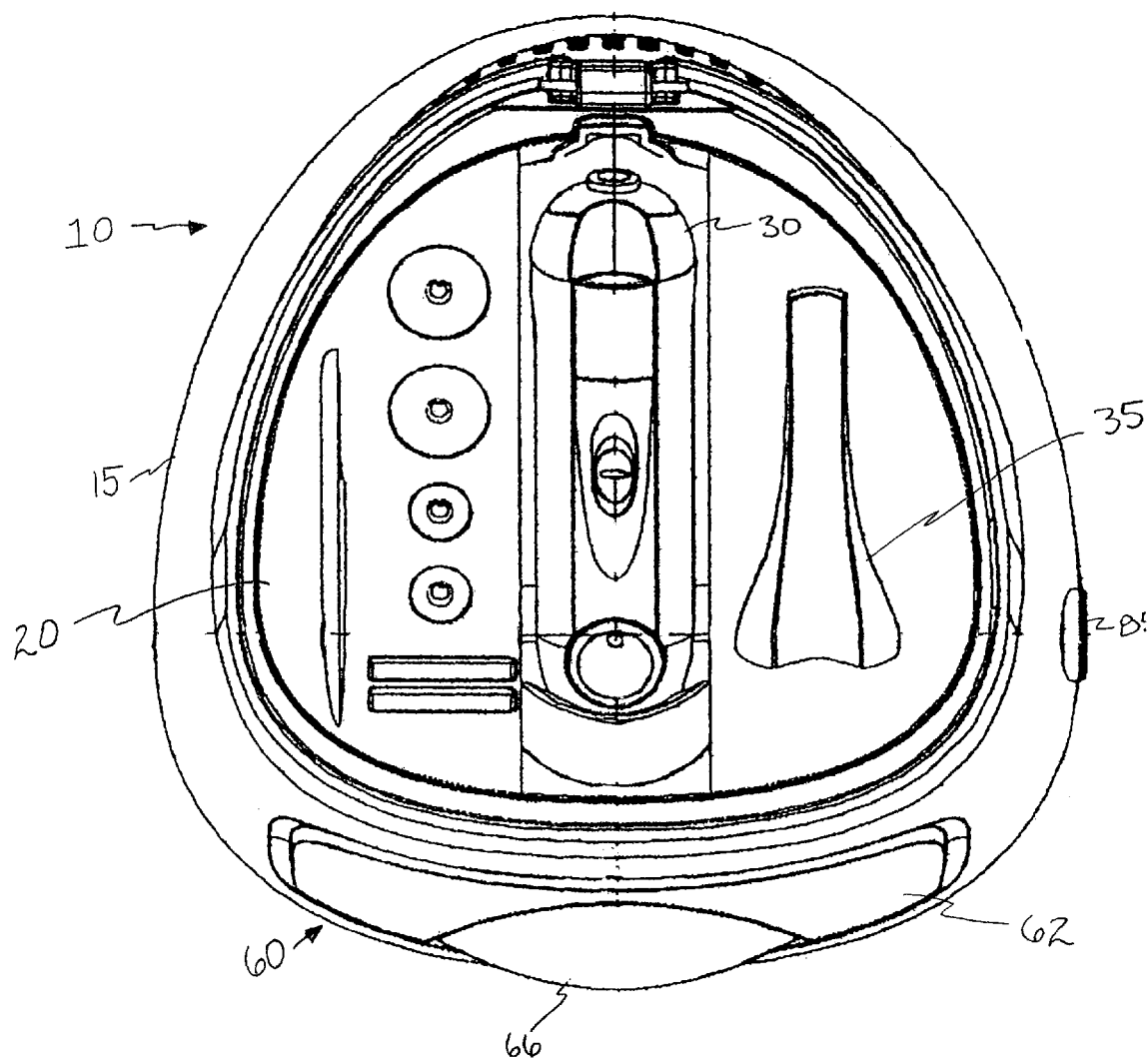
FIG. 2 is a top view of a nail care system having a base housing for storing a hand tool, at least a rotary motion adapter head and a linear motion adapter head for use with the hand tool, a number of nail care attachments, and a manicure bowl, in accordance with the present invention.
Figure 3:
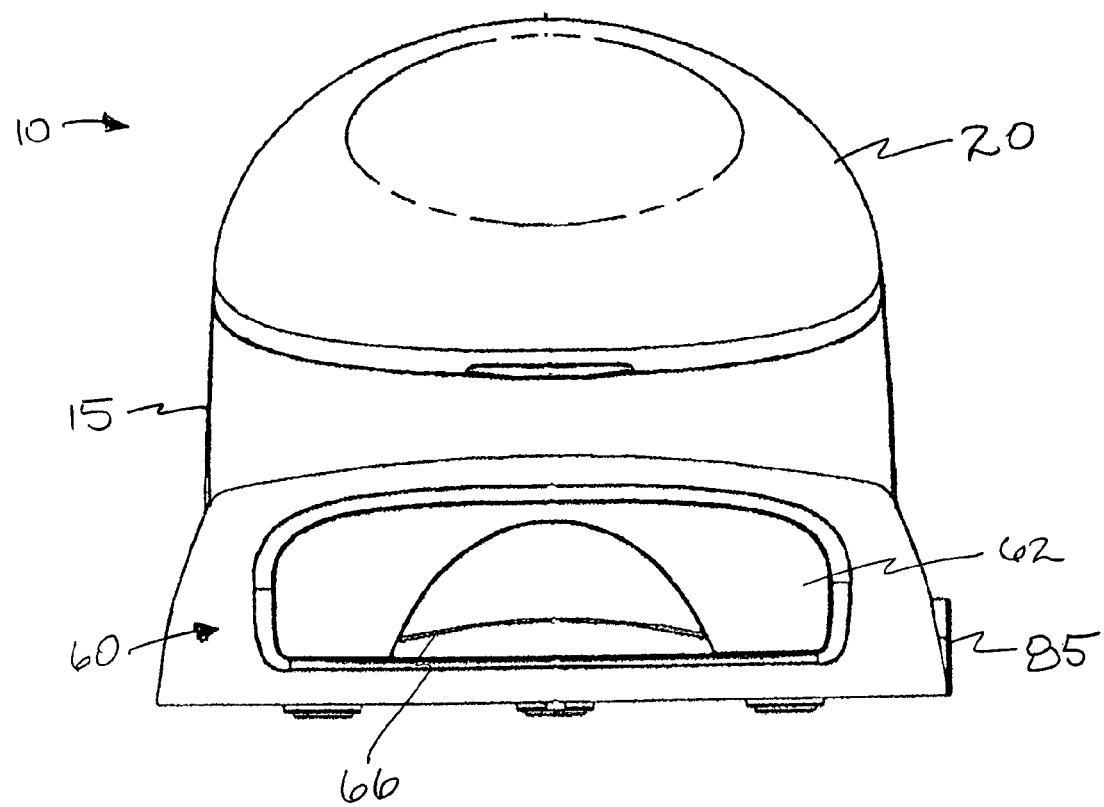
FIG. 3 is a front view of the nail care system of FIG. 2.
Figure 4:
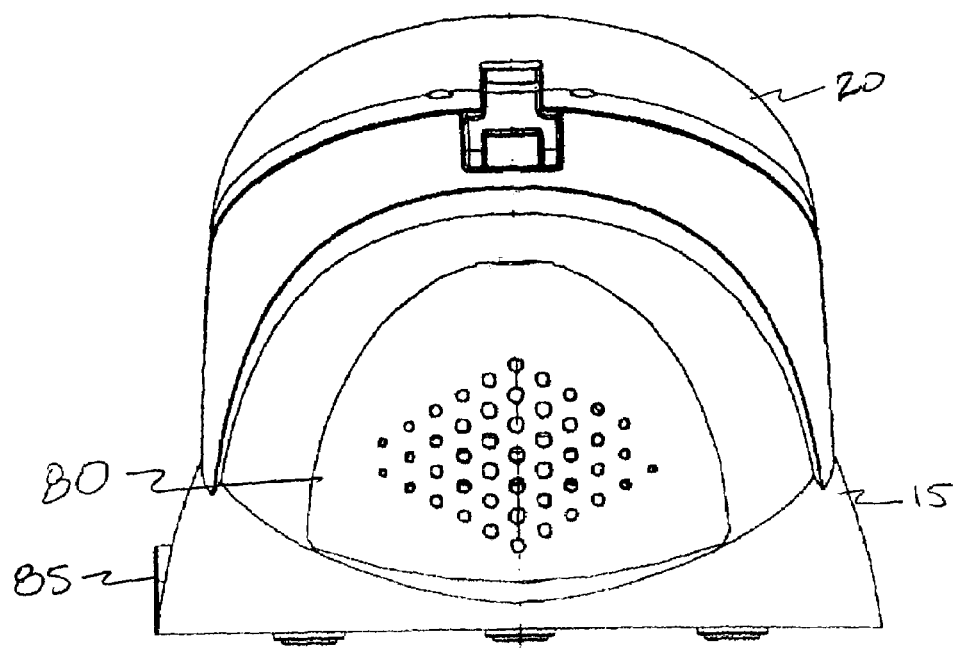
FIG. 4 is a rear view of the nail care system of FIG. 2.
Figure 5:
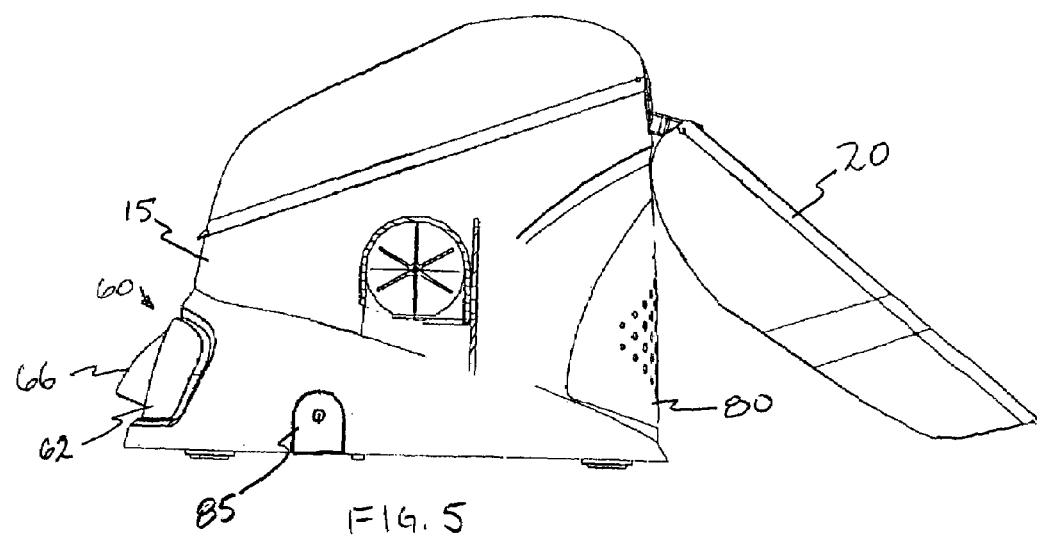
FIG. 5 is a side view of the nail care system of FIG. 2, shown with the lid thereof in an open position.
Figure 9:
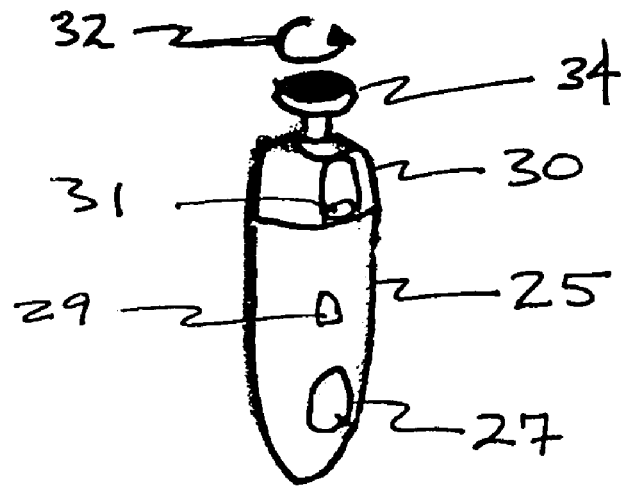
FIG. 9 is a depiction of the powered hand tool of FIGS. 1 and 2 interfaced with the rotary motio adapter head of FIGS. 8A and 8B.
Figure 10:
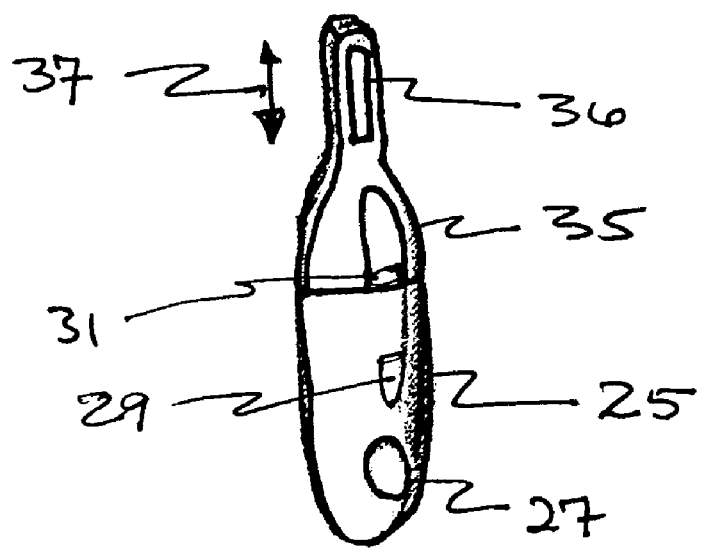
FIG. 10 is a depiction of the powered hand tool of FIGS. 1 and 2 interfaced with the linear motion adapter head of FIGS. 7A and 7B.

In FIGS. 1, 2, and 9, rotary motion adapter head 30 is shown connected to hand tool 25. In FIGS. 1 and 2, linear motion adapter head is shown stored in an adapter head storage compartment of base housing 15, whereas in FIG. 10 linear motion adapter head 35 is shown attached to hand tool 25.

Rotary motion adapter head 30, when connected to hand tool 25, provides a rotary motion to a nail care attachment, for example buffer 34, attached thereto. FIGS. 11A and 11D depict exemplary rotary grinders for shaping and filing of nails. FIGS. 11B and 11C depict exemplary rotary buffers for polishing and buffing nails. Motion arrow 32 indicates an exemplary rotary motion imparted to the nail care attachment by rotary motion adapter head 30.

Linear motion adapter head 35, when connected to hand tool 25, provides a linear motion to a nail care attachment, for example polisher 36, attached thereto. FIGS. 11F and 11G depict exemplary linear motion buffers for polishing and buffing nails. FIG. 11E depicts an exemplary cuticle pusher for manipulating the cuticle of a nail. Motion arrow 37 indicates the exemplary linear motion (e.g., oscillation) imparted by linear head 35.

In yet another aspect of the present invention, a nail dryer is provided. The nail dryer function of the present invention is preferably provided by operation of a fan (not shown) internal to base housing 15 that disperses, preferably, heated air onto a user's nails placed within base housing cavity 65. The nail dryer is accessible via the opening to compartment 65. That is, the hand of a user is placed inside of compartment 65, when manicure bowl 60 is removed, so that the nails are selectively exposed to the heated air circulating therewithin. Operation of the nail dryer function is preferably controlled via a nail dryer selector 75 in or on base housing 15. The heating aspect of the hand dryer may be provided by a radiant heater. The heater may also encompass a infrared heater or other types of heat therapy such as, but not limited to, heated stones.

Base housing 15 preferably includes an UV (ultraviolet) light selector 70. UV light selector 70 provides operational control of a UV light source (not shown) that is preferably located in base housing 15. The UV light source is accessible via the opening of compartment 65. In this manner, the hand of a user is placed inside of compartment 65 whereby the hand is selectively exposed to the therapeutic effects of UV light therapy.

Hand tool 25 preferably includes a light switch 29 for controlling operation of a light source 31 located on hand tool 25. Light source 31 may be an incandescent light bulb, an LED, or any other suitable light source. Light source 31 may be selectively controlled by light switch 29 to illuminate the workspace area, hand or foot, being worked by hand tool 25.

In an aspect of the present invention, the speeds at which rotary motion adapter 30 and linear motion adapter 35 operate are preferably variable and selectively adjustable. Accordingly, a variable speed dial control 27 is provided on hand tool 25 for selectively controlling the speed at which rotary motion adapter 30 rotates attachments interfaced therewith, and the speed at which linear motion adapter 35 linearly oscillates. The speed may preferably be varied in a series of distinct steps, for example ten, or continuously variable.

Preferably, located within or above compartment 65 is the dryer fan. Above the fan is the heater, with the nail care attachments storage compartment located above the heater. Thus, the vertical arrangement of the nail care attachments, storage compartment, heater, fan, and compartment 65 provides the space saving design of nail care system 10.

In another aspect of the present invention, base housing 15 stores the substantially elongated hand tool 25 in a vertical (i.e., upright) position, as shown in FIG. 1. In FIG. 2, hand tool 25 is supported by base housing 15 at an angle, not in a horizontal position. The vertical and angled storage position allows base housing 15 to provide storage compartments for hand tool 25, the various nail care attachments (e.g., twelve), coiled cord 50, multiple adapter heads 30 and 35, manicure bowl 60, and the AC power cord in a very compact, self-contained nail care system. The vertical configuration aspect of base housing 15 provides for this efficient, space saving aspect of this nail care system.

The functions and controls discussed above are exemplary of the nail care system of the present invention and do not preclude the inclusion, exclusion, and combination of other nail care system functions and controls.

It should also be appreciated by those skilled in the art that the particular nail care system functions and other aspects of the teachings herein are but examples of the present invention. Thus, they do not limit the scope or variety of applications that the present invention may be suitably implemented. It should be understood that the foregoing description is only illustrative of a present implementation of the teachings herein. Various alternatives and modification may be devised by those skilled in the art without departing from the invention. Accordingly, the present invention is intended to embrace all such alternatives, modifications, and variances.

I claim:

1. A nail care system comprising:
A manicure bowl having a front wall, a side wall, and a floor cooperating with each other to define an interior space for retaining fluid therein; a hand tool adapted to being powered; a plurality of adapter heads for interfacing with said hand tool; a base housing having an aperture and defining a cavity there through, said manicure bowl being removably received within said cavity and the base housing further having a storage compartment for storing said powered hand tool and said plurality of motion adapter heads; a fan disposed in an interior space of said base housing for circulating air in said cavity, wherein said fan being located directly above said manicure bowl.

2. The nail care system of claim 1, further comprising a lid for covering at least an upper portion of said storage compartment.

3. The nail care system of claim 2, wherein said lid is at least partially translucent.

4. The nail care system of claim 2, wherein said lid is hingedly connected to said base housing.

5. The nail care system of claim 1, wherein said floor of said manicure bowl is contoured to support a hand and fingers.

6. The nail care system of claim 1, wherein said manicure bowl is selectively received in said cavity such that said front wall of said manicure bowl is flush with an exterior surface of said base housing at an interface between said front wall and said exterior surface of said base housing.

7. The nail care system of claim 1, wherein one of said plurality of adapter heads is a linear motion adapter head and another of said plurality of adapter heads is a rotary motion adapter head.

* * * * *